(12) United States Patent
Dennerlein et al.

(10) Patent No.: US 8,213,564 B2
(45) Date of Patent: Jul. 3, 2012

(54) METHOD AND APPARATUS FOR DETERMINING AN IMAGE FROM X-RAY PROJECTIONS RECORDED WHEN TRAVERSING A TRAJECTORY

(75) Inventors: Frank Dennerlein, Forchheim (DE); Holger Scherl, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 104 days.

(21) Appl. No.: 12/888,121

(22) Filed: Sep. 22, 2010

(65) Prior Publication Data

US 2011/0069807 A1 Mar. 24, 2011

(30) Foreign Application Priority Data

Sep. 24, 2009 (DE) .................. 10 2009 042 922

(51) Int. Cl.
*A61B 6/03* (2006.01)
(52) U.S. Cl. .................. 378/4; 378/15; 382/131
(58) Field of Classification Search .............. 378/4–20; 382/131
See application file for complete search history.

(56) References Cited

U.S. PATENT DOCUMENTS

| 6,771,733 | B2 | 8/2004 | Katsevich |
| 7,403,587 | B2 | 7/2008 | Bontus et al. |
| 2008/0089468 | A1* | 4/2008 | Heigl et al. .................. 378/20 |
| 2009/0016592 | A1* | 1/2009 | Hoppe et al. .................. 382/131 |

FOREIGN PATENT DOCUMENTS

DE 10 2008 031 530 A1 1/2009

OTHER PUBLICATIONS

Hoppe et al., Truncated correction for oblique filtering lines, available on line Nov. 24, 2008, Medical Physics, vol. 35, No. 12, pp. 5910-5920.*
German Office Action dated Sep. 8, 2010 for corresponding German Patent Application No. DE 10 2009 042 922.0 with English translation.
Katsevich, Alexander, "Image Reconstruction for the Circle and Line Trajectory," Phys. Med. Biol., vol. 49, 2004, pp. 5059-5072.
Katsevich, Alexander, "Image Reconstruction for the Circle-and-Arc Trajectory," Phys. Med. Biol., vol. 50, 2005, pp. 2249-2265.
Katsevich, Alexander, "Theoretically Exact Filtered Backprojection-Type Inversion Algorithm for Spiral CT," SIAM J. Appl. Math., vol. 62, No. 6, 2002, pp. 2012-2026.

(Continued)

*Primary Examiner* — Edward Glick
*Assistant Examiner* — John Corbett
(74) *Attorney, Agent, or Firm* — Lempia Summerfield Katz LLC

(57) ABSTRACT

A method for determining attenuation coefficients for an object using a movable x-ray source and a detector for recording projections is provided. The method includes defining a trajectory for the movable x-ray source, defining filtering lines for the filtering of projection data, and defining positions on the filtering lines, at which the projection derivative is to be formed using a mathematical algorithm for a back-projection. The method also includes defining sampling positions on the trajectory, traversing, by the x-ray source, the trajectory and recording a projection for each sampling position. Projection derivatives with respect to the trajectory path are calculated numerically for each of the positions directly on the filtering lines, and using a mathematical algorithm, attenuation coefficients are determined for the object from the calculated projection derivatives, for the reconstruction.

16 Claims, 3 Drawing Sheets

OTHER PUBLICATIONS

Noo, Frédéric et al., "Exact Helical Reconstruction Using Native Cone-Beam Geometries," Phys. Med. Biol., vol. 48, 2003, pp. 3787-3818.

Noo, Frédéric et al., "A New Scheme for View-Dependent Data Differentiation in Fan-Beam and Cone-Beam Computed Tomography," Phys. Med. Biol., vol. 52, 2007, pp. 5393-5414.

Pack, Jed D. et al., Cone-Beam Reconstruction Using 1D Filtering Along the Projection of $M$-lines, Inverse Problems, vol. 21, 2005, pp. 1105-1120.

Yu, Hengyong et al., "Feldkamp-Type VOI Reconstruction from Super-Short-Scan Cone-Beam Data," Med. Phys., vol. 6, 2004, pp. 1357-1352.

* cited by examiner

METHOD AND APPARATUS FOR DETERMINING AN IMAGE FROM X-RAY PROJECTIONS RECORDED WHEN TRAVERSING A TRAJECTORY

This application claims the benefit of DE 10 2009 042 922.0, filed Sep. 24, 2009.

BACKGROUND

The present embodiments relate to a method and an apparatus for determining attenuation coefficients for an object using a movable x-ray source and a detector.

X-ray methods are standard methods in medical technology. In the case of simple x-ray recordings, x-ray radiation is transmitted through an object to be examined and is then recorded by a detector. The recording or projection represents an item of information about the attenuation of the transmitted x-rays on a path through the object. The attenuation of the x-ray radiation depends on the density of the parts of the object, through which the x-ray radiation is radiated. The density supplies information about the nature of the object, which may be shown in visual form for diagnoses. For an x-ray recording, the intensity registered by the detector depends on the overall composition of the object on the line along which the x-rays pass (e.g., data integrated over a line is available). Attenuation coefficients may not be obtained for the object from one x-ray recording as a function of all three spatial coordinates. For a three-dimensional image, a plurality of x-ray recordings is made from different recording positions. From the plurality of x-ray recordings, a three-dimensional image is reconstructed. One of the most important technologies in medical technology that takes this approach is computer tomography (CT). As part of the CT, the x-ray source and the x-ray detector traverse a path or trajectory. In doing this, recordings are made along the trajectory. From these recordings, a three-dimensional image is reconstructed from attenuation coefficients that are associated with the density.

Image reconstruction in transmission computer tomography is a complex mathematical problem. For the construction of three-dimensional images, two groups of methods have become established: exact methods (cf. Katsevich, A., "Theoretically Exact FBP-Type Inversion Algorithm for Spiral CT," *SIAM J. Appl. Math.*, Vol. 62, No. 6 (2002): pp. 2012-26; Katsevich, A., "Image Reconstruction for the Circle-and-Line Trajectory," *Phys. Med. Biol.*, Vol. 49, No. 22 (2004): pp. 5059-72; Katsevich, A., "Image Reconstruction for the Circle-and-Arc Trajectory," *Phys. Med. Biol.*, Vol. 50, No. 10 (2005): pp. 2249-65; and Pack, J. and F. Noo, "Cone-Beam Reconstruction Using 1D Filtering Along the Projection of M-Lines," *Inverse Problems*, Vol. 21, No. 3 (2005): pp. 1105-20); and approximative methods (cf. Yu, H. and G. Wang "Feldkamp-type VOI reconstruction from super-short-scan cone-beam data," *Med. Phys.*, Vol. 31, No. 6 (2004): pp. 1357-62). These may be (theoretically) exact methods that contain no mathematical approximations; the numeric implementation and the technical realization may, however, involve errors.

These methods calculate the 3D density distribution of the object under examination from 2D projection data, essentially taking into account the following acts: (i) calculation of the numeric derivative of the projections recorded along the sample path of the x-ray source (see Noo, F., et al., "A New Scheme for View-Dependent Data Differentiation in Fan-Beam and Cone-Beam Computed Tomography," *Phys. Med. Biol.*, Vol. 52, No. 17 (2007): pp. 5393-414 for various possibilities), (ii) 1-D displacement-invariant filtering of the differentiated projection data along a family of filter lines, and (iii) weighted back-projection of the filtered projections into the image volume.

In practical applications, the projection data is not available in continuous form, but in discrete form because, the result of the data recording is a finite number of projection images, each of which is available in sampled form. During the reconstruction, interpolation steps therefore occur. The interpolations may have a negative effect on the quality of the resulting reconstructed image (e.g., in that the interpolations limit the maximum achievable spatial resolution).

Until now, reconstruction methods have been implemented such that interpolation operations are performed during the calculation of the derivatives, the filtering and the back-projection. Between the individual calculation steps, the results are held in temporary storage. The calculation of the numeric derivative is performed such that the results are obtained at the original detector positions, even though the derivatives are required at other positions, determined by the filtering lines during the filtering. An interpolation is used if the derivative is calculated on a Cartesian grid, but the filtering lines are not parallel to the axes of the grid. In this case, the filtering lines for the Feldkamp method discussed in "Feldkamp-type VOI reconstruction from super-short-scan cone-beam data" run along horizontal lines in the x-ray image detector. With the newer approximative and exact reconstruction methods discussed in the references above, in conjunction with new types of sampling paths such as, for example, circle-and-line, circle-and-arc and saddle, the filtering lines used are mostly non-horizontal.

Interpolation may be used both in the calculation of the derivative and also in the extraction of the filtering lines on the projection images. The extraction of the filtering lines may be critical for the image quality (e.g., spatial resolution), for which reason improved interpolation methods have been proposed (Joseph's method; see Noo, F., et al., "Exact helical reconstruction using native cone-beam geometrics," *Phys. Med. Biol.*, Vol. 48, No. 23 (2003): pp. 3787-818) in order to minimize the loss of image quality.

SUMMARY AND DESCRIPTION

The present embodiments may obviate one or more of the drawbacks or limitations in the art. For example, the quality of image reconstruction in reconstruction methods may be improved, and the image reconstruction may be structured more efficiently.

In accordance with the present embodiments, attenuation coefficients for an object are determined using a movable x-ray source and a detector, where the detector records projections. In doing this, a trajectory is defined for the movable x-ray source. For the filtering of projection data, filtering lines are defined. The filtering lines may or may not be straight lines. In one embodiment with non-flat or non-planar detectors, the filtering is effected along curves (or lines) lying on the detector.

In accordance with the present embodiments, positions, at which the projection is to be differentiated using a mathematical algorithm for a back-projection, are defined on or along the filtering lines. Sampling positions on the trajectory are defined. The sample positions may be defined on the basis of the defined positions on the filtering lines. In doing this, account is taken of the fact that the derivatives of the trajectory are determined for the positions on the filtering lines. The sampling positions may be determined such that when the derivatives are formed numerically, the resulting derivatives are precisely at defined positions on the filtering lines.

If existing external conditions (e.g., the form of the trajectory, characteristics of the detector) make it so that sampling positions may not be defined for a numerical formation of derivatives that are precisely at defined positions on the filtering lines, the sampling positions may be defined so that the interpolation that is used may be effected with a high (numerical) accuracy. For example, the sampling positions are defined such that the corresponding numerical derivatives lie close to positions on the filtering line.

The trajectory is traversed by the x-ray source, and a record is made of a projection for each sampling position. The projection may be given by the values of the radiation intensity recorded by detector elements. The traverse of the trajectory may be made at a constant speed to avoid oscillations in the source. The recorded values of the radiation intensity are used directly for the numerical calculation of projection derivatives relative to the path of the trajectory for each of the positions on the filtering lines. The term "directly" may be use of a relationship that establishes a direct connection between an approximation and the values of the radiation intensity in the calculation of the projection derivatives and no use of any derivatives at other positions. The conventional interpolation of derivative values, used for filtering, to obtain the derivative values at the positions on the filtering lines is avoided. In this way, the accuracy of the method is increased. In addition, in accordance with the present embodiments, derivatives are only determined for the positions on the filtering lines. This approach is less resource intensive than conventional methods, which determine derivatives for all the sampling points of the detector or for a grid that covers the detector area.

The attenuation coefficients for the object are determined for the reconstruction from the calculated projection derivatives using a (theoretically exact or approximative) mathematical algorithm.

An apparatus for carrying out the methods of the present embodiments may be realized using software, hardware and firmware. Special hardware such as, for example, FPGA technology, ASIC technology, DSP solutions and special processors (e.g., a cell broadband engine, or graphics accelerators) may be used.

DETAILED DESCRIPTION OF THE DRAWINGS

Figure 1:
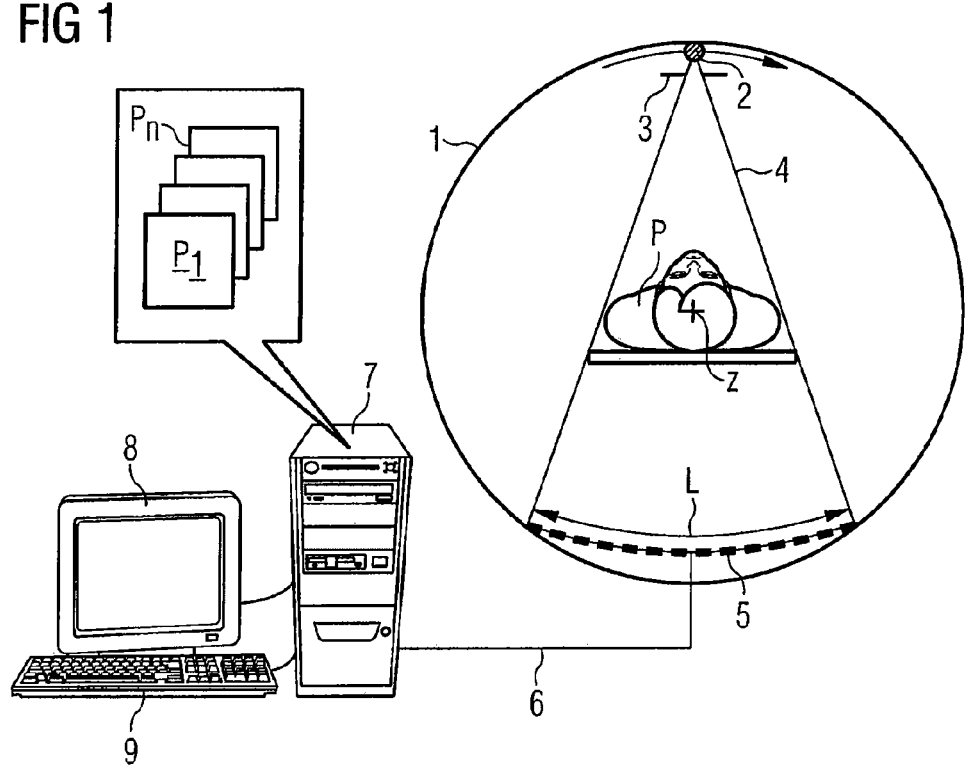
FIG. 1 is a schematic view of a spiral CT device having a plurality of rows of detector elements, viewed in the z-direction.
Figure 2:
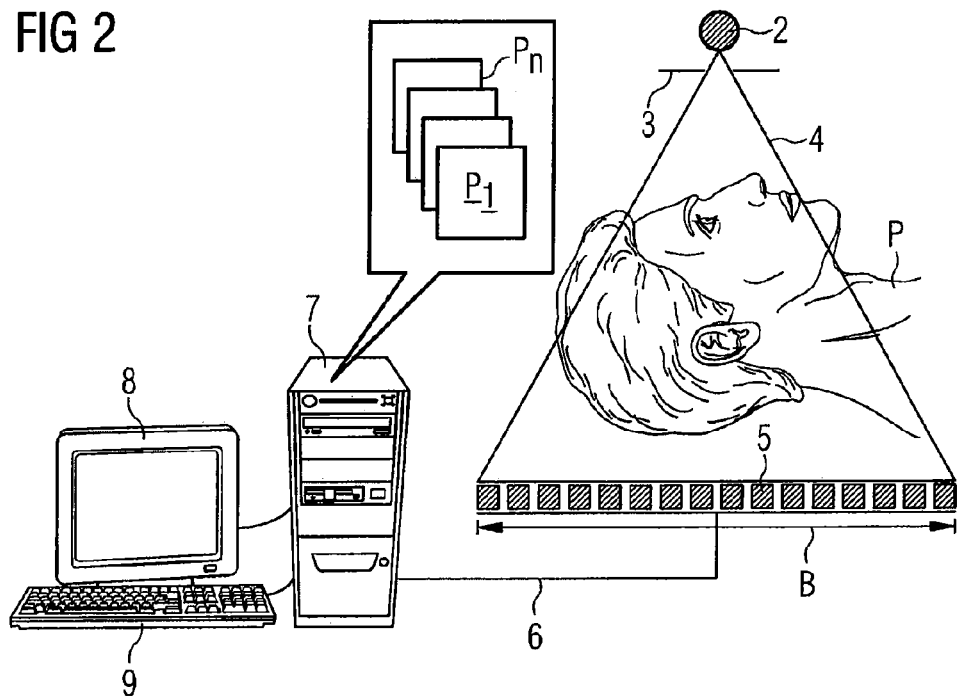
FIG. 2 is a longitudinal section through the device shown in FIG. 1, along the z-axis.
Figure 3:
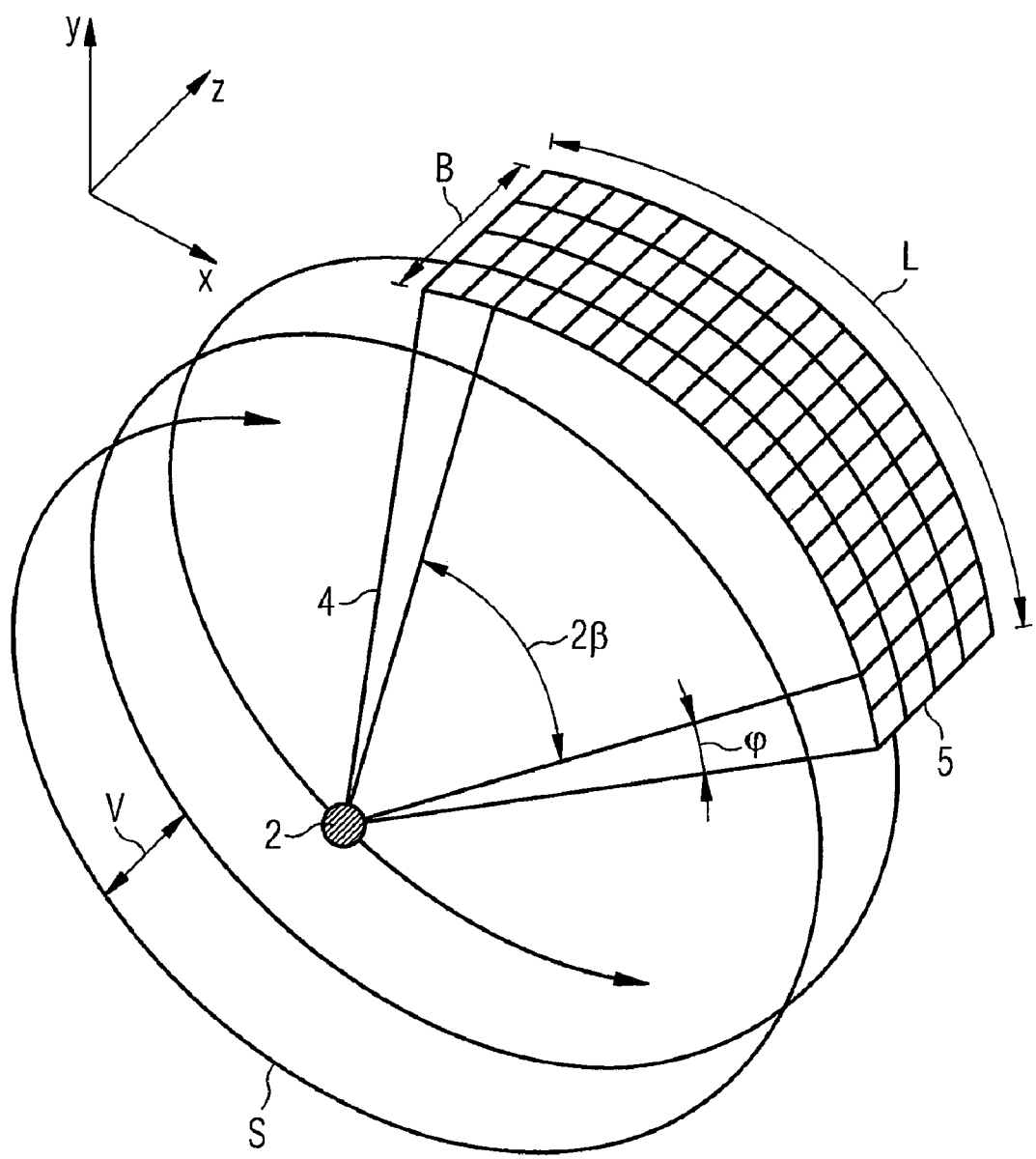
FIG. 3 is a schematic view of the spiral-shaped movement of a focus and a detector.

FIGS. 1 and 2 show a spiral CT device with a multi-row detector, suitable for carrying out the methods of the present embodiments. FIG. 1 shows a section perpendicular to the z-axis through a gantry 1 with a focus 2, and a detector 5 (with width B and length L) that also rotates. FIG. 2 shows a longitudinal section in the direction of the z-axis. The gantry 1 has an x-ray source with a focus 2 and a beam shutter 3 located in front of the focus 2 and close to the x-ray source. From the focus 2, a bundle of rays 4, limited by the beam shutter 3, passes to the detector 5 on the opposite side, penetrating through the patient P lying between the focus 2 and the detector 5. Sampling is carried out during rotation of the focus 2 and the detector 5 about the z-axis, where the patient P is at the same time moved in the direction of the z-axis. This results in a spiral path S for the focus 2 and the detector 5 in the coordinate system of the patient P, with a rate of 'climb' or advance V, as shown spatially and schematically in FIG. 3.

During the sampling of the patient P, dosage-dependent signals sensed by the detector 5 are transmitted via a data/control line 6 to a computational unit 7. From raw data measured, and using known methods that are stored in the program modules $P_1$ to $P_n$, the spatial structure of the region of the patient P that has been sampled is computed in the known way with respect to absorption values of the region. In accordance with the present embodiments, a theoretically exact reconstruction method is used to do this.

The remaining operation and control of the CT device is carried out using the computational unit 7 and a keyboard 9. The computed data may be output via a monitor 8 or a printer, which is not shown.

A modern reconstruction method is described in, for example, Pack, J. and F. Noo, "Cone-Beam Reconstruction Using 1D Filtering Along the Projection of M-Lines," *Inverse Problems*, Vol. 21, No. 3 (2005): pp. 1105-20, Noo, F., et al., "A New Scheme for View-Dependent Data Differentiation in Fan-Beam and Cone-Beam Computed Tomography," *Phys. Med. Biol.*, Vol. 52, No. 17 (2007): pp. 5393-414, Noo, F., et al., "Exact helical reconstruction using native cone-beam geometrics," *Phys. Med. Biol.*, Vol. 48, No. 23 (2003): pp. 3787-818 or in U.S. Pat. No. 6,771,733 B2. The specification of U.S. Pat. No. 6,771,733 B2 gives a reconstruction formula (formula 10) that is well suited to the numerical implementation of an exact method. For implementation, formula 10 may use a further transformation, according to the path or trajectory used. For a spiral path, the appropriate formula is reproduced, for example, as formula 29 in U.S. Pat. No. 6,771,733 B2. FIG. 2 in U.S. 6,771,733 B2 describes the typical sequence of a reconstruction using a formula of that type. In act 30 (or FIG. 4, in which act 30 is shown in more detail) the determination is described for filtering lines. In act 40, an interpolation is carried out for the purpose of calculating derivatives for positions on the filtering lines. This is where the present embodiments take effect. The extraction of derivative values that are used along the filtering lines is avoided by adapting the calculation of the derivatives to the position of the filtering lines. The sampling positions for the filtering lines are determined in the original projection image. After the sampling positions are determined, the numerical derivative is calculated at the sampling positions. This is described in detail below with reference to FIGS. 4-7.

Figure 4:
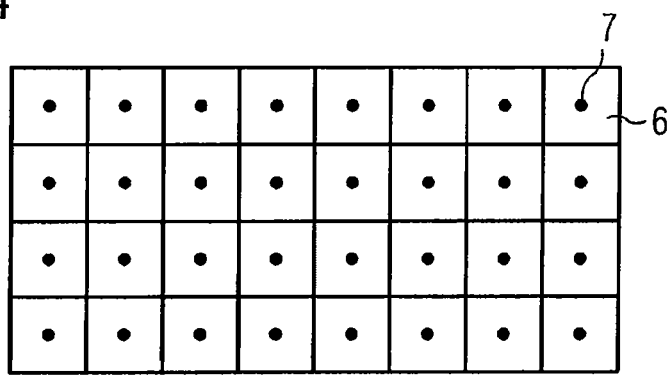
FIG. 4 shows a conventional projection image.

FIG. 4 shows a conventional projection image with detector elements 6. Sampling points 7 for the detector elements are identified by a dot symbol (black dot).

Conventionally, a derivative with respect to the trajectory (e.g., a derivative with respect to a parameter that parameterizes the trajectory or path) is calculated numerically for the sampling positions.

Figure 5:
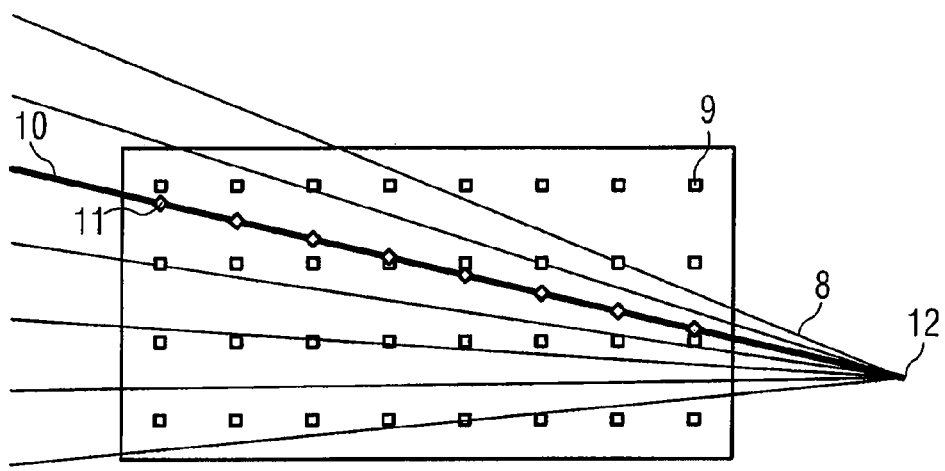
FIG. 5 shows a conventional projection image with filtering lines.

As shown in FIG. 5, filtering lines 8 are determined. Sampling points 9, at which numeric derivatives have been calculated, are identified by squares. Shown by way of example is a filtering line 10, on which positions 11 are shown as diamonds. The derivatives are determined at the positions 11 (e.g., for a back-projection using, for example, formula 10 in U.S. Pat. No. 6,771,733 B2). The determination of the derivatives is effected using interpolation (e.g., by an approximation).

Figure 6:
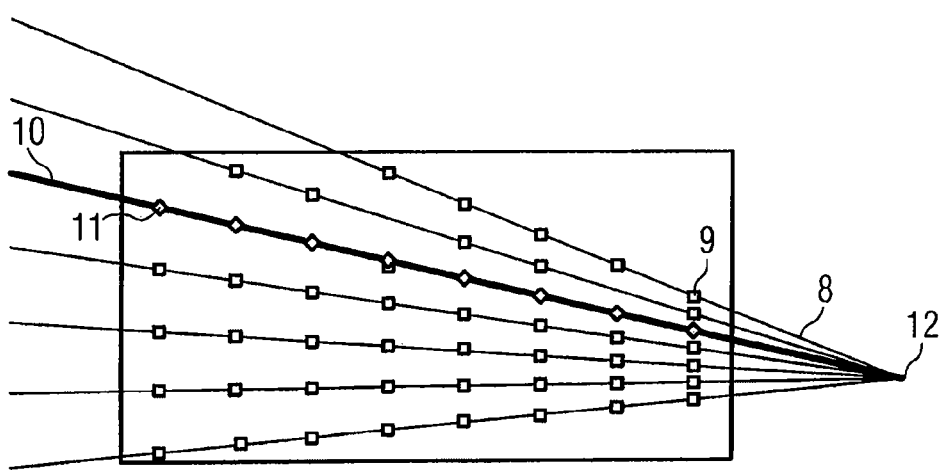
FIG. 6 shows a projection image when one embodiment of a method for determining attenuation coefficients is applied.

This approximation or interpolation is avoided using the present embodiments. This is shown in FIG. 6. The numeric derivatives are calculated directly for the derivative values on the filtering line (e.g., from the projections recorded).

The present embodiments permit the derivative values to be calculated at the positions in the filtered projection image. As before, the derivative is approximated in the course of the numeric calculation, but the interpolation used with the extraction of the values on the filtering lines is eliminated. The present embodiments supply optimal numeric derivative values at the sampling positions on the filtering lines. An improvement in the image quality is thereby achieved.

In addition, the present embodiments allow the numeric derivatives to be restricted to places on the filtering lines. This eliminates the sampling in regions of the projection image that contain no filtering lines (e.g., the region on the top right in FIG. 6) or regions in which no derivatives are used due to truncation of the filtering lines (cf. DE 102008031530 A1). This leads to fewer samplings, and may thereby produce improved run-time performance by comparison with conventional methods (depending on the number of filtering lines).

The present embodiments are not restricted to the exemplary embodiment described but may be applied with other reconstruction methods that use filtering lines.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining attenuation coefficients for an object using a movable x-ray source and a detector for recording projections, the method comprising:
    defining a trajectory for the movable x-ray source;
    defining filtering lines for the filtering of projection data;
    defining positions on the filtering lines, at which a projection derivative is to be formed using a mathematical algorithm for a back-projection;
    defining sampling positions on the trajectory;
    traversing along the trajectory with the x-ray source and recording a projection for each of the sampling positions, wherein the projection comprises radiation intensity values recorded by detector elements;
    directly calculating, using the recorded radiation intensity values, the projection derivatives with respect to the trajectory path for each of the positions on the filtering lines; and
    determining, from the calculated projection derivatives, attenuation coefficients for the object for the reconstruction, using a mathematical algorithm.

2. The method as claimed in claim 1, wherein the sampling positions on the trajectory are defined based on the defined positions on the filtering lines.

3. The method as claimed in claim 2, wherein the detector is planar.

4. The method as claimed in claim 2, wherein the filtering lines are not parallel.

5. The method as claimed in claim 2, wherein the trajectory is traversed by the movable x-ray source at a constant speed.

6. The method as claimed in claim 1, wherein the detector is planar.

7. The method as claimed in claim 6, wherein the filtering lines are not parallel.

8. The method as claimed in claim 6, wherein the trajectory is traversed by the movable x-ray source at a constant speed.

9. The method as claimed in claim 1, wherein the filtering lines are not parallel.

10. The method as claimed in claim 9, wherein the trajectory is traversed by the movable x-ray source at a constant speed.

11. The method as claimed in claim 1, wherein the trajectory is traversed by the movable x-ray source at a constant speed.

12. An apparatus for determining attenuation coefficients for an object, the apparatus comprising:
    a movable x-ray source;
    a detector for recording projections; and
    a processor configured to:
        define a trajectory for the movable x-ray source;
        define filtering lines for the filtering of projection data;
        define positions on the filtering lines, at which a projection derivative for a back projection is to be determined by a mathematical algorithm;
        define sampling positions on the trajectory based on the defined positions on the filtering lines;
        numerically calculate a projection derivative with respect to the trajectory path for each of the positions on the filtering lines; and
        determine, from the calculated projection derivatives, attenuation coefficients for the object for a reconstruction, using a mathematical algorithm,
    wherein the movable x-ray source is operable to traverse along the trajectory, and
    wherein the detector is operable to record a projection for each sampling position.

13. The apparatus as claimed in claim 12, wherein the detector is planar.

14. The apparatus as claimed in claim 13, wherein the sampling positions are defined in groups, and
    wherein a group of sampling positions is provided for the numeric calculation of the projection derivative at a position.

15. The apparatus as claimed in claim 12, wherein the sampling positions are defined in groups, and
    wherein a group of sampling positions is provided for the numeric calculation of the projection derivative at a position.

16. The apparatus as claimed in claim 15, wherein the spacing of the sampling positions within the group is based on the accuracy of the numeric calculation of the derivatives.

* * * * *